United States Patent [19]

Gerhardt

[11] Patent Number: 5,156,162
[45] Date of Patent: Oct. 20, 1992

[54] SCOLIOSIS MEASUREMENT INSTRUMENT WITH MIDLINE LEG MEMBER

[76] Inventor: John J. Gerhardt, 15650 SE. Oatfield Rd., Milwaukie, Oreg. 97267

[21] Appl. No.: 751,920

[22] Filed: Aug. 29, 1991

[51] Int. Cl.$^5$ ............................................. A61B 5/103
[52] U.S. Cl. ................................... 128/781; 33/512
[58] Field of Search ............... 128/781, 774, 775, 776, 128/777, 778, 779, 780, 782; 33/512, 513, 514, 515

[56] References Cited

U.S. PATENT DOCUMENTS

| 1,571,140 | 1/1926 | O'Connor | 128/781 |
| 2,930,133 | 3/1960 | Thompson | 33/512 |
| 4,444,204 | 4/1984 | Bryant et al. | 128/781 |

FOREIGN PATENT DOCUMENTS

| 2407704 | 7/1979 | France | 128/781 |
| 685277  | 9/1979 | U.S.S.R. | 128/781 |
| 1326244 | 7/1987 | U.S.S.R. | 128/781 |

OTHER PUBLICATIONS

ISOMED "Universal Caliper (Uni-Cal)" information sheet. Date unknown.

Primary Examiner—Max Hindenburg
Assistant Examiner—Guy V. Tucker
Attorney, Agent, or Firm—Olson & Olson

[57] ABSTRACT

A scoliosis measurement instrument includes the elongated scale bar and fixed and adjustable legs of a universal caliper, an inclinometer mounted on the adjustable leg, and a scoliosis midline rod located at the center mark of a bi-directional distance scale on the scale bar. The fixed leg is movable along the scale bar for positioning its skin contact tip over either the highest point of the rib hump or lumbar bulge or the opposite valley of a subject being examined, and the adjustable leg is movable along the scale bar for positioning at the same but opposite distance from the center mark of the bi-directional scale. The adjustable leg also is movable normal to the scale bar to distances of its skin contact tip from the scale bar greater or less than the distance of the fixed leg tip from the scale bar, to measure the distance between the highest prominence and opposite valley. An inclinometer is mounted on the base of the adjustable leg for measuring the rotational deformities of the spine by setting the adjustable leg over the left and the fixed leg over the right posterior/superior iliac spine while holding the tip of the scoliosis midline rod over the midline. This sets the lateral distances of the caliper legs for measuring rotation of the thoracic spine.

6 Claims, 2 Drawing Sheets

SCOLIOSIS MEASUREMENT INSTRUMENT WITH MIDLINE LEG MEMBER

BACKGROUND OF THE INVENTION

This invention relates to spinal measurements, and more particularly to an attachment for a universal caliper by which to facilitate scoliosis measurements.

Measurements of lateral curvature of the spine heretofore have been dependent upon X-rays for accuracy with the inherent risk of possibly harmful exposure to radiation, especially in the most vulnerable age of puberty and adolescent lifespan. The surface measurements were lacking accuracy and reproducibility and required use of rather expensive instrumentation each designed for one specific use. For this reason, they have been used mainly in research institutions and few scoliosis centers. The majority of investigators used only visual estimations of distances and angles. Reproducibility and followup could not be achieved because no accurate parameters had been established.

SUMMARY OF THE INVENTION

This invention provides for scoliosis measurements by attaching to the horizontal, bi-directional scale bar of a universal caliper a midline spinal process indicator from the center scale position of which the vertically fixed leg and vertically adjustable leg of the caliper may be precisely located.

It is the principal objective of this invention to provide for scoliosis measurements which avoid the aforementioned risks, disadvantages and limitations of prior methods and means.

Another objective of this invention is the provision of a scoliosis measurement attachment for a universal caliper by which to enable the easy, but precise and reproducible measurements of lateral spine curvature accessible to the majority of clinicians evaluating and treating spinal deformities of the growing child and adolescent.

Still another objective of this invention is the provision of a scoliosis measurement attachment for a universal caliper, which attachment is configured to avoid interference with normal operations of the universal caliper.

A further objective of this invention is to provide a scoliosis measurement attachment for a universal caliper, which attachment is of simplified construction for economical manufacture.

A still further objective of this invention is to provide a scoliosis measurement instrument by combining with a conventional universal caliper a midline spinal process indicator for enabling the precise location of the fixed and adjustable legs of the caliper.

A still further objective of this invention is the provision of scoliosis measurement instrument of simplified construction for economical manufacture.

The foregoing and other objects and advantages of this invention will appear from the following detailed description, taken in connection with the accompanying drawings of a preferred embodiment.

DESCRIPTION OF THE PREFERRED EMBODIMENT

Figure 1:
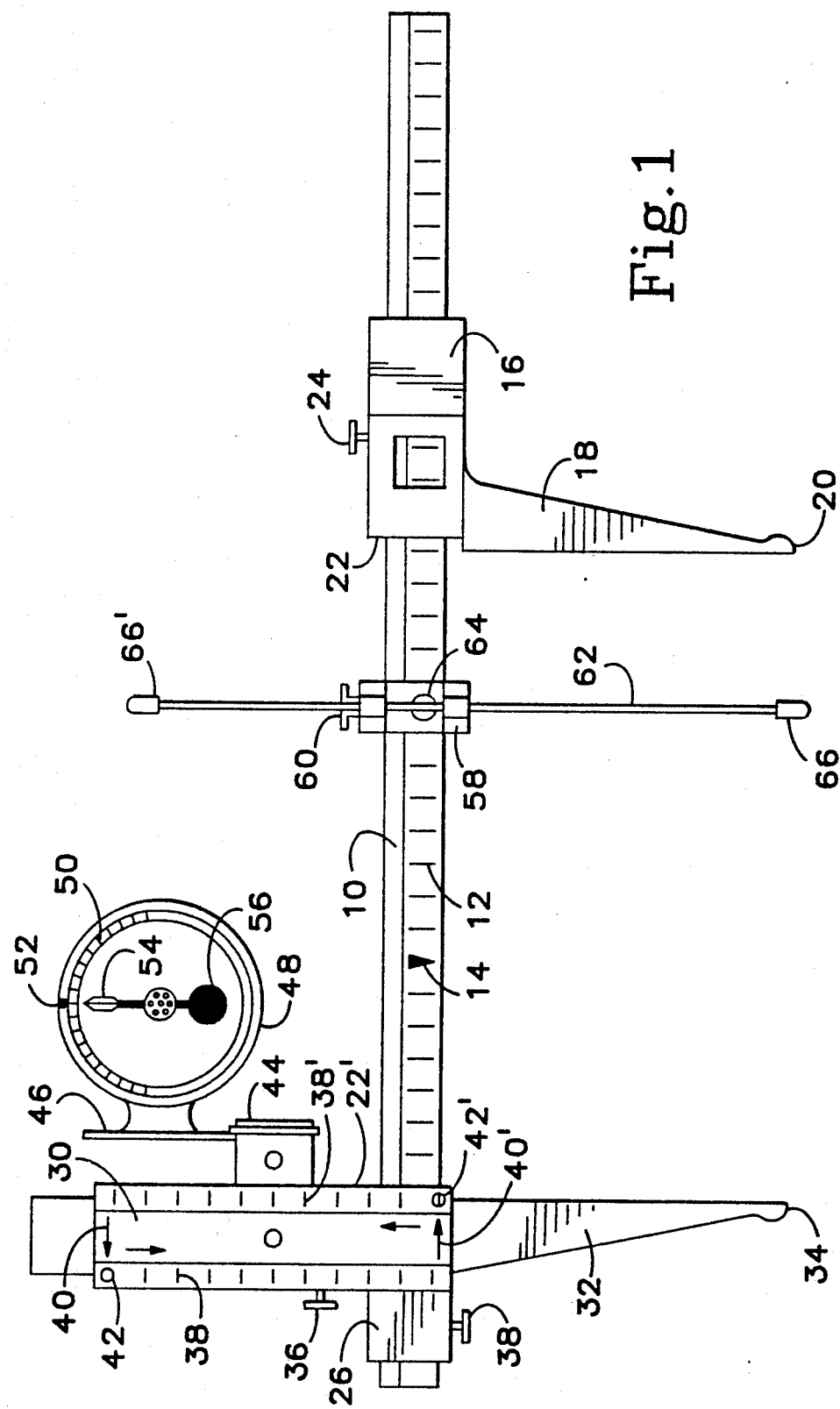
FIG. 1 is a front elevational view of a scoliosis measurement instrument embodying the features of this invention.

The scoliosis measurement instrument of this invention utilizes a conventional universal caliper and inclinometer. The universal caliper includes an elongated scale bar 10 upon which is provided a bi-directional distance scale 12 extending in opposite directions from a center mark 14.

A fixed leg support base 16 has a longitudinal opening therethrough for reception of the scale bar 10, whereby to afford sliding movement of the base 16 along the bar. The base supports an elongated fixed leg member 18 which extends normal to the longitudinal opening in the base and hence perpendicular to the longitudinal dimension of the bar 10. The outer end of the leg member 18 is formed or fitted with a contact tip 20 for engaging the skin surface of a body being examined.

The base 16 is provided with an index pointer for cooperative association with the scale 12 for indicating distance positions of the base 16, and hence the inner side edge of leg 18 from the center mark 14. In the embodiment illustrated, the index pointer is provided by the inner end edge 22 of the base 16.

A set screw 24 on the base 16 is arranged for engagement with the scale bar 10 for securing the base releasably to the bar in selected positions of adjustment along the bar toward and away from the center mark 14.

The scale bar 10 also slidably mounts an adjustable leg support base 26, by means of a longitudinal opening through the base. Set screw 28 on the base is arranged for engagement with the scale bar for securing the base releasably to the bar in selected positions of adjustment along the bar, toward and away from the center mark 14.

Integral with or otherwise secured to the base 26 and extending perpendicular to the longitudinal opening through the base, and hence perpendicular to the bar 10, is a guide member 30. In the embodiment illustrated, the guide member is substantially C-shaped in cross section, thus forming a pair of spaced grooves for sliding reception of the opposite longitudinal sides of an elongated adjustable leg member 32. The leg member is provided at one end with a contact tip 34 for engaging the skin surface of a body being examined. The inner side edge 22' of the guide member 30 functions as an index pointer for cooperative association with the scale 12 for indicating distance positions of the inner side edge of leg 32 from the center mark 14.

A set screw 36 on one side of the guide member 30 is arranged for releasable engagement with the adjustable leg member 32 for securing the latter in selected positions of adjustment along the guide member, and hence selected positions of adjustment of the contact tip 34 toward and away from the scale bar 10.

A distance scale 38 is provided on one vertical side of the guide 30 for association with an index pointer 40 on the leg 32 for indicating the distance of the contact tip 34 from the scale bar 10 as the leg 32 is moved downwardly from the position shown in FIG. 1. As illustrated in FIG. 1, the zero mark 42 of scale 38 is positioned so that when the index pointer 40 registers therewith, the contact tips 20 and 34 are located the same distance from the scale bar 10. This position is also identified by releasably engaging detents on the guide 30 and leg 32.

A second distance scale 38' is provided on the other vertical side of the guide 30 for association with a second index pointer 40' on the leg 32 for indicating the distance of the contact tip 34 from the scale bar 10 as the leg is moved upwardly from the position shown in FIG. 1, When the index pointer 40' registers with the zero mark 42' the contact tips 20 and 34 are the same distance from the scale bar 10. This arrangement of scales maximizes the range of adjustment of the leg 32.

The scales 12 and 38 may be graduated to indicate distances in metric or U.S. units, such as centimeters or inches, respectively.

Figure 2:
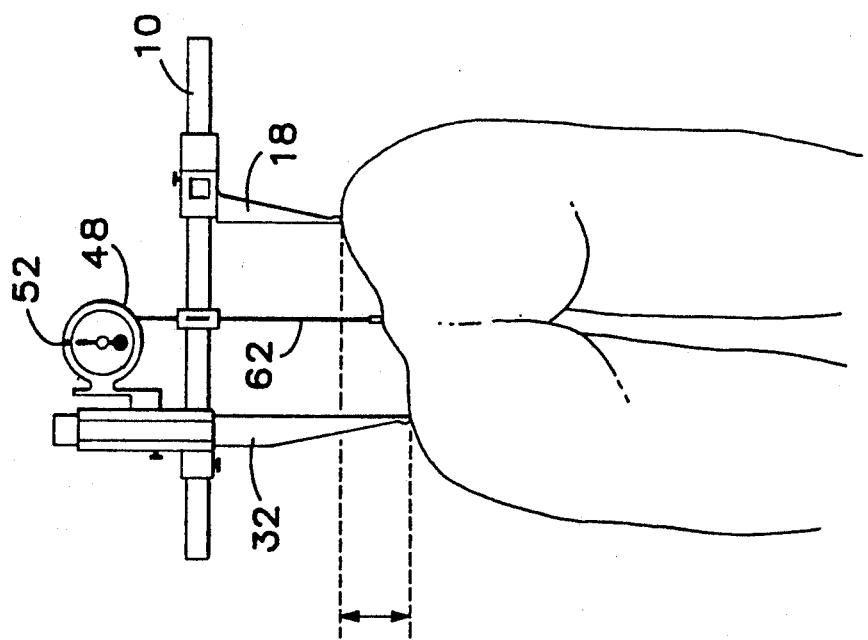
FIG. 2 is a front elevational view of the instrument of FIG. 1 in operative position for measuring the vertical distance between a rib hump and the opposite valley.

Although FIG. 2 shows the leg 32 moved downward relative to the zero mark 42, because the valley is on the left side, the leg 32 may be moved upward relative to zero mark 42' when the valley is on the right side and the hip hump is on the left side.

An inclinometer is operatively mounted on the scale bar 10 for indicating angular dispositions of the scale bar relative to horizontal. In the embodiment illustrated, a support block 44 is secured to the guide member 30 and is configured to removably support the base 46 of an inclinometer case 48. A graduated, bi-directional degree scale 50 on the case extends in opposite directions from a zero mark 52 and is associated with an index pointer 54 on a pivoted gravity weight 56, to give indication of angular inclination of the scale bar 10 relative to horizontal.

The foregoing structural assembly is well known as an instrument which affords precise measurements of vertical and horizontal distances, leg length discrepancies, heel lifts, inside and outside diameters, tilts, inclinations, rotations, torsions, supination/pronation, eversion/inversion and other parameters.

In accordance with this invention, means is provided for association with the foregoing assembly to facilitate the precise and reproducible measurements of scapular and shoulder deviations, rib humps, lumbar bulges, pelvic tilts and rotational deformities of the spine. The means provided for this purpose is illustrated herein as a scoliosis midline leg support base member 58 provided with a longitudinal opening for slidably receiving the scale bar 10. A set screw 60 on the base member serves to secure the latter releasably to the scale bar at the position of the center mark 14.

An elongated scoliosis midline leg member 62, illustrated in the drawing as a rod, is supported by the base member 58 in position disposed substantially in the common plane of the fixed and adjustable legs 18 and 32, respectively. The rod 62 extends slidably through spaced openings in the base member 58. An opening 64 in the base member 58 serves to expose the scale 12 to view, to facilitate locating the rod 62 in registry with the center mark 14.

A contact tip 66 is provided on the lower end of the rod 62 for engaging the skin surface of a body being examined. A second contact tip 66' on the upper end of the rod limits the downward movement of the rod relative to the base member 58.

The structural assembly which includes the scoliosis rod 62 is utilized for scoliosis measurements, as follows:

The body of the subject to be examined is prepared by identifying the necessary anatomical and bony landmarks. This is accomplished by having the subject stand upright with knees locked and feet spaced apart about 15 cm (6 inches). Marks then are applied to the skin to identify the spinal process of C7 (vertabra prominence), the roots of the scapula spines, the distal angles of the scapula, the highest point of the iliac crest, and the posterior/superior iliac spines.

The subject now is asked to bend forward with knees straight. For screening purposes, marks then are applied to the skin to identify the spinal processes of T1, T4, T8, T12, L3, and S1, as well as the highest points of the rib hump and the lumbar bulge at the above levels. For a complete test, marks are applied at the spinal processes at each vertabral level.

Measurement of distances now is accomplished by having the subject bend forward. With reference to FIG. 2, the instrument is adjusted to secure the scoliosis rod 62 at the center mark 14 on the scale bar 10. With the scale bar 10 disposed in a horizontal plane, by keeping the inclinometer pointer 54 on the zero mark of scale 52, the midline rod tip 66 is placed over the spinal process and the fixed leg 18 is moved to place the tip 20 over the highest point of the rib hump at the T8 level. The fixed leg base 16 is secured by set screw 24 and the lateral distance between the center mark 14 and the fixed leg index pointer 22 is read. The adjustable leg then is moved to place the index mark 40 at the same distance on the opposite side of the center mark 14, and secured to the scale bar 10 by set screw 28.

Keeping the scale bar 10 horizontal, the adjustable leg 32 is moved vertically downward to bring the tip 34 into contact with the skin at the valley of the back opposite the rib hump. The distance on the vertical scale 38 from the zero mark 42 to the index mark 40 then is read.

The foregoing procedure is repeated for each desired level of the chosen screening or complete test.

Figure 3:
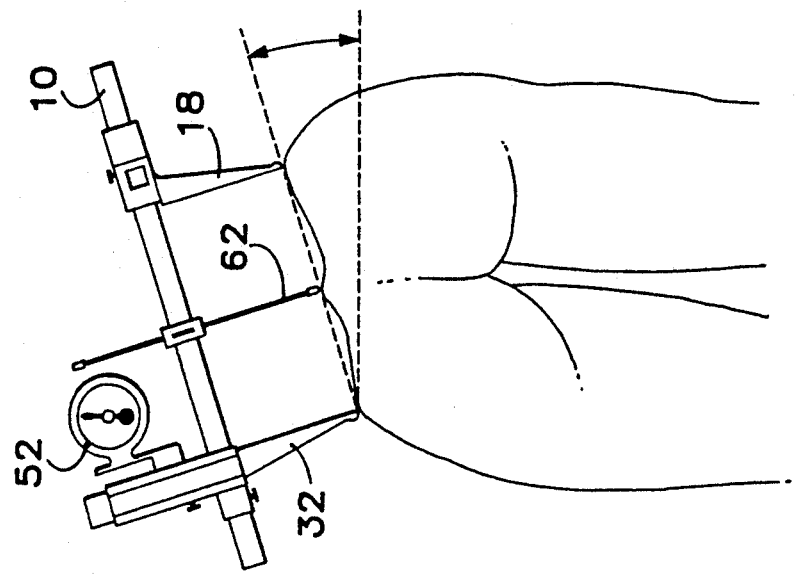
FIG. 3 is a front elevational view of the instrument of FIG. 1 in operative position for measuring angles of rotation relative to a rib hump and the opposite valley.

Measurement of rotational deformities of the spine is achieved by setting both caliper legs 18 and 32 at the same vertical distance from the scale bar 10 (FIG. 3), placing the midline indicator rod tip 66 over the midline of the sacrum, the adjustable leg tip 34 over the left, and the fixed leg tip 20 over the right, posterior/superior iliac spine. The distance from the midline to the leg 18 on the side of maximal prominence is measured and recorded in the appropriate column of a scoliosis chart. The base 16 is secured to bar 10 by set screw 24. The leg 32 then is set at the same distance from center mark 14 as leg 18 but on the opposite side of the center mark, and secured by set screw 28. The instrument then is brought over the T8 level with the midline indicator tip 66 over the T8 spinal process and the leg tips 20 and 34 on the rib hump and valley, respectively. The tip 34 of the adjustable leg 32 then is placed on the skin at the valley of the back opposite the rib hump or lumbar bulge. The distances of the index pointers 22 and 40 from the center mark 14 are read and the rotational angle is read on the inclinometer. The foregoing procedure is repeated for each desired level of the chosen screening or complete test.

When measuring rotation deformity at the lumbar spine (lumbar bulge), the lateral distances of the caliper legs from the center mark 14 are reduced by 1 cm each.

Since all scoliosis measurements are precise and reproducible, monitoring and evaluation of progress of treatment is facilitated by use of an appropriately arranged scoliosis chart to record all distances and angular measurements during each test.

It will be apparent to this skilled in the art that various changes may be made in the structural details described hereinbefore without departing from the spirit of this invention and the scope of the appended claims.

I claim:
1. A scoliosis measurement instrument, comprising:
   a) an elongated scale bar having thereon a bi-directional graduated distance scale extending longitudinally in opposite directions from a center mark,
   b) a fixed leg member mounted on the scale bar for longitudinal movement relative to said scale bar on one side of the center mark of said bi-directional scale, the fixed leg member extending perpendicular to the longitudinal axis of said scale bar,
   c) an adjustable leg member mounted on the scale bar for longitudinal and perpendicular movements relative to said scale bar on the side of said center mark opposite said fixed leg member,
   d) the adjustable leg member having thereon a distance scale extending perpendicular to the scale bar, and
   e) a scoliosis midline leg member mounted on the scale bar at the center mark of said bi-directional scale between said fixed and adjustable leg members for movement freely in the direction perpendicular to the longitudinal axis of the scale bar for engaging one of its ends against the skin surface of a body being examined.

2. The scoliosis measurement instrument of claim 1 wherein the adjustable leg member includes a base member mounted slidably on the scale bar, a guide member on the base member, and an elongated leg mounted on the guide member for movement perpendicular to the scale bar, the distance scale being on one of the said guide member and leg and an index pointer being on the other of said guide member and leg.

3. The scoliosis measurement instrument of claim 1 wherein the distance scale on the adjustable leg member comprises a pair of parallel scales extending in opposite directions from associated zero marks, and a pair of index pointers on the adjustable leg associated one with each scale.

4. The scoliosis measurement instrument of claim 1 wherein the scoliosis midline leg member includes a base member mounted on the scale bar, and an elongated rod supported by the base member for adjustable movement perpendicular to the scale bar.

5. The scoliosis measurement instrument of claim 1 including an inclinometer operatively mounted on the scale bar for indicating angular dispositions of the scale bar relative to horizontal and for indicating the horizontal position of the scale bar.

6. The scoliosis measurement instrument of claim 5 including an inclinometer support member mounted on the adjustable leg guide member and configured to removably support the inclinometer.

* * * * *